United States Patent [19]

Torihara et al.

[11] Patent Number: 4,837,351

[45] Date of Patent: Jun. 6, 1989

[54] 2-CYANO-4-PHENYL PENTANE AND FRAGRANCE OR PERFUME COMPOSITIONS CONTAINING THE SAME

[75] Inventors: Masahiro Torihara, Niigata; Yoshin Tamai, Shibata, both of Japan

[73] Assignee: Kuraray Company Ltd., Kurashiki, Japan

[21] Appl. No.: 127,381

[22] Filed: Dec. 2, 1987

[30] Foreign Application Priority Data

Dec. 29, 1986 [JP] Japan .................................. 61-310913

[51] Int. Cl.$^4$ ............................................ C07C 121/46
[52] U.S. Cl. ............................................ 558/388; 512/6
[58] Field of Search ............................ 558/388; 512/6

[56] References Cited

U.S. PATENT DOCUMENTS

| | | | |
|---|---|---|---|
| 4,193,934 | 3/1980 | Bauer et al. | 558/388 |
| 4,458,699 | 7/1984 | Schreck et al. | 131/276 |
| 4,459,224 | 7/1984 | Van der Weerdt et al. | 558/388 |

FOREIGN PATENT DOCUMENTS

| | | |
|---|---|---|
| 0076493 | 4/1983 | European Pat. Off. . |
| 2308735 | 8/1974 | Fed. Rep. of Germany . |

*Primary Examiner*—William R. Dixon, Jr.
*Assistant Examiner*—Jerry D. Johnson
*Attorney, Agent, or Firm*—Oblon, Fisher, Spivak, McClelland & Maier

[57] ABSTRACT

Described is a new chemical, 2-cyano-4-phenyl pentane, and the fragrance or perfume compositions containing said 2-cyano-4-phenyl pentane, in which the aroma of said 2-cyano-4-phenyl pentane is effectively imparted.

10 Claims, No Drawings

2-CYANO-4-PHENYL PENTANE AND FRAGRANCE OR PERFUME COMPOSITIONS CONTAINING THE SAME

BACKGROUND OF THE INVENTION (1) Field of the Invention

The present invention relates to a new chemical, 2-cyano-4-phenyl pentane, and fragrance or perfume compositions containing the same.

(2) Description of the Related Art

It has not been reported any characteristics of 2-cyano-4-phenyl pentane as an aroma chemical (fragrance) because of a new chemical.

It is desirable to provide a new aroma chemical (fragrance), which impart a different ordor note, modify, augument or enhance the fragrances of known aroma chemicals (fragrances), to give a change on the fragrances or perfumes.

SUMMARY OF THE INVENTION

It is an object of the invention to provide 2-cyano-4-phenyl pentane of the following formula:

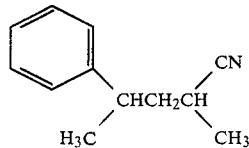

2-cyano-4-phenyl pentane of this invention is a new chemical which has not appeared in literature yet. 2-cyano-4-phenyl pentane has a powerful fresh, fruity, floral odor note accompanied by a citrus green top note and is thus of value as an ingredient to be compounded with a fragrance or a fragrance composition which has a fruity, floral odor note, such as mughet, lilac, gardenia, rose, violet, grape-fruit, yuzu (citrus junos) or the like. Accordingly, it is an another object of the invention to provide a fragrance or perfume composition containing an olfactorily sensible amount of 2-cyano-4-phenyl pentane.

The fragrance or perfume compositions provided by the present invention have high quality and modern odor notes, making effective use of the fragrances or perfumes of 2-cyano-4-phenyl pentane as mentioned above, and also deepen the floral ordor notes of other aroma chemicals (fragrances) compounded with 2-cyano-4-phenyl pentane as shown in the following examples.

It has been reported that 2-methyl-4-phenyl pentanal, substituted the cyano group of 2-cyano-4-phenyl pentane with formyl group, publicly known before the application of this invention, has green floral and earthy aroma (odor) (U.S. Pat. No. 4,458,699). 2-cyano-4-phenyl pentane of the present invention, being differing from that of said 2-methyl-4-phenyl pentanal, as mentioned above, gives perfumes and fragrance or perfume compositions having deep odor notes making effective use of these aromas.

DESCRIPTION OF THE PREFERRED EMBODIMENTS

The effective proportions of 2-cyano-4-phenyl pentane for the desired perfuming effects or perfume compounding effects are between about 0.1 to 95% (by weight) of the total weight of the fragrance or perfume composition, preferrably between about 1 to 25% (by weight).

The fragrance or perfume composition of the present invention can be used in a large variety of ways. For example, it can be used as space odorants; perfumes; bath preparations; hair preparations such as hair tonics, pomades, hair liquids, hair creams, stick pomades etc.; hair cleaners, such as shampoos, rinses etc.; cleaners; detergents and the like. In addition, the fragrance or perfume compositions can be used for imparting an odor to technical products such as textile fibers and fabrics or paper products.

For example, 2-cyano-4-phenyl pentane can be produced by the following synthetic route:

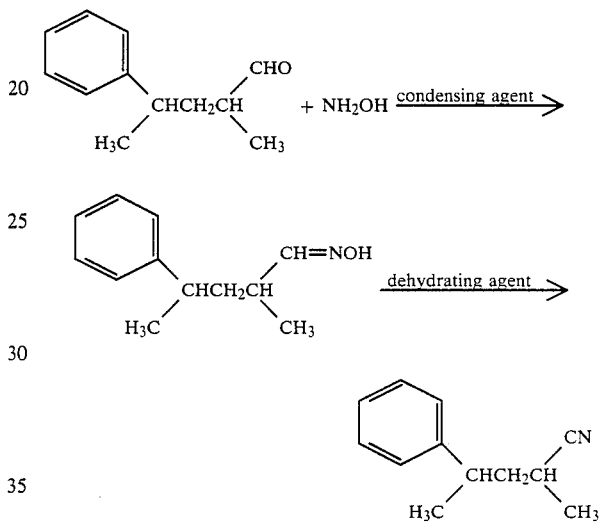

Hydroxyl amine is generally used in an amount of from about 1.0 to 2.0 moles per mole of 2-methyl-4-phenyl pentanal in the condensation reaction of 2-methyl-4-phenyl pentanal and hydroxyl amine. Examples of suitable condensing agent include mineral acids, such as hydrochloric acid, sulfuric acid and organic acids, such as acetic acid and the like in acidic condition, and carbonate, organic acid salt or hydroxide of alkali or alkali-earth metal, and ammonia in alkaline condition. Examples of suitable solvent include water, mixed solvents of water and alcohols, such as methanol, ethanol and the like. The reaction can be generally conducted at temperatures ranging from about −20° C. to about 100° C. The reaction times can be ranging from about one to dozens of hours depending on condensing agents, solvents and reaction temperature.

Preferable examples of dehydrating agents in the dehydration reaction of 2-methyl-4-phenyl pentanal oxime mentioned above include acetic anhydride, acetic anhydride with sodium acetate, thionyl chloride, phosphorous pentaoxide, phosporous pentachloride, benzoyl chloride and the like. The reaction is conducted in the presence or absence of a solvent. Examples of suitable solvents include pyridine, benzene, ethyl ether and the like. The reaction can be generally conducted at temperatures ranging from room temperature to about 150° C. The reaction times can be ranging from about one to a few hours depending on dehyrating agents, solvents and reaction temperature. The seperation and purification of 2-cyano-4-phenyl pentane from reaction mixture can be conducted as that of products in general organic synthesis reaction, such as distillation or the like.

EXAMPLES

The present invention will now be described with reference to the following examples.

Production Example (Synthesis of 2-cyano-4-phenyl pentane)

In a three-necked flask of 1-liter in volume, equipped with a thermometer, a stirrer and a stopper was placed 230 g (1.32 mol) of 2-methyl-4-phenyl pentanal, 100 g (1.44 mol) of hydroxyl amine hydrochloride, and 300 ml of water, and stirred at room temperature. To the whole mixture, 90 g (0.78 mol) of sodium carbonate anhydride was added for one hour and was stirred for one overnight. The reaction mixture is extracted with 200 ml of isopropyl ether, followed by washing the organic layer with saturated sodium chloride aqueous solution. The isopropyl ether was distilled out under reduced pressure to give 270 g of oil. This oil was subjected to GLC analysis, revealing that it was 2-methyl-4-phenyl pentanal oxime of about 95% purity.

In a four-necked flask of 1-liter in volume equipped with a thermometer, a reflux condenser, a dropping funnel and a stirrer, was placed 270 g of this obtained 2-methyl-4-phenyl pentanal oxime, and was added in dropwise 270 g of acetic anhydride, and then the mixture was stirred at 140° C. for 2 hours. The reaction mixture was then cooled and poured into 1-liter of water, followed by the extraction with 300 ml of isopropyl ether. The separated organic layer of the reaction mixture was washed with 100 ml of 10% sodium hydroxide aqueous solution two times and 100 ml of saturated sodium chloride aqueous solution two times. After the removal of isopropyl ether by a rotary evaporator, the residue was subjected to a refined distillation to give 180 g of distillate (90°-95° C./1.5 mmHg). The physical data of this product are as follows:

CI-MS (M+ calculated value 173)

$^1$H-NMR ($\delta$, TMS Standard, CDCl$_3$ solution)

1.24, 1.33 (3H each, both d, J=7.7Hz)

1.50-2.20 (2H, m)

2.52, 2.92 (1H each, both tq, J=7.7, 7.7Hz)

7.10-7.49 (5H, m)

This product was acertained as 2-cyano-4-phenyl pentane by these analytical data.

Formulation Example 1

5 parts by weight of 2-cyano-4-phenyl pentane was compounded with 95 parts by weight of fragrance or perfume composition of the following formula having a mughet odor note.

|  | Parts by weight |
| --- | --- |
| Hydroxycitronellal | 20 |
| Phenyl ethyl alcohol | 15 |
| Linalyl acetate | 10 |
| Terpineol | 5 |
| Benzyl acetate | 5 |
| Geraniol | 5 |
| Linalool | 10 |
| Citronellol | 8 |
| Hexyl cinnamic aldehyde | 3 |
| Ylang ylang oil | 2 |
| Geranium oil | 2 |
| α-ionone | 3 |
| Jasmin.absolute | 2 |
| Heliotropine | 2 |
| Musk ketone | 3 |

Thus obtained fragrance or perfume composition has a deep floral odor with muguet note as compared with the fragrance or perfume composition without 2-cyano-4-phenyl pentane. Furthermore, the fragrance or perfume of 2-cyano-4-phenyl pentane well harmonizes with other fragrance ingredients.

Formulation Example 2

8 parts by weight of 2-cyano-4-phenyl pentane was compounded with 92 parts by weight of fragrance or perfume composition of the following formula having gardenia odor note.

|  | Parts by weight |
| --- | --- |
| Methyl phenyl carbinyl acetate | 5 |
| Dimethyl benzyl carbinol | 10 |
| Hydroxycitronellal | 10 |
| Bergamot | 5 |
| Nerol | 5 |
| Benzyl acetate | 10 |
| Phenyl ethyl alcohol | 10 |
| Methyl ionone | 5 |
| Linalool | 10 |
| Tolu Balsam | 3 |
| Heliotropine | 3 |
| Jassmin.absolute | 2 |
| Rose.absolute | 2 |
| Galbanum oil | 3 |
| Vetiver oil | 3 |
| Sandalwood oil | 2 |
| Vanillin | 2 |
| Musk ketone | 2 |

Thus obtained fragrance composition has a deep floral odor with gardenia note as compared with the fragrance composition without 2-cyano-4-phenyl pentane. Furthermore, the fragrance of 2-cyano-4-phenyl pentane well harmonizes with other fragrance ingredients.

Formulation Example 3

5 Parts by weight of 2-cyano-4-phenyl pentane was compounded with 95% by weight of fragrance composition of the following formula having a rose odor note.

|  | Parts by weight |
| --- | --- |
| Phenyl ethyl alcohol | 20 |
| Geraniol | 20 |
| Citronellol | 8 |
| Linalool | 5 |
| Benzyl acetate | 5 |
| α-ionone | 3 |
| Terpineol | 2 |
| Cinnamic alcohol | 2 |
| Rhodinol | 5 |
| Geranium oil | 5 |
| Eugenol | 2 |
| Nerol | 3 |
| Aldehyde C-10 (10%) | 2 |
| Nerolidol | 5 |
| Guaiac lard | 2 |
| Rose.absolute | 3 |
| Musk ketone | 3 |

Thus obtained fragrance composition has a deep rose odor note as compared with the fragrance composition without 2-cyano-4-phenyl pentane. Furthermore, the fragrance of 2-cyano-4-phenyl pentane well harmonizes with other frangrance ingredients.

Formation Example 4

15 parts by weight of 2-cyano-4-phenyl pentane was compounded with 85 parts by weight of fragrance or perfume composition of the following formula having a fruity floral note.

|                      | Parts by Weight |
|----------------------|-----------------|
| Phenyl ethyl alcohol | 15              |
| Benzyl acetate       | 10              |
| Geraniol             | 5               |
| Linalool             | 5               |
| Terpineol            | 3               |
| Orange oil           | 15              |
| Lemon oil            | 10              |
| Mandarin oil         | 5               |
| Citral               | 1               |
| Petitgrain oil       | 3               |
| Aldehyde-10 (10%)    | 2               |
| Cis-3-hexane-1-ol    | 1               |
| Bergamot oil         | 2               |
| Nerol                | 2               |
| Hydroxycitronellal   | 3               |
| Methyl ionone        | 2               |
| Galbanum oil         | 1               |

Thus obtained fragrance composition has a deep fruity floral odor notes as compared with the fragrance composition without 2-cyano-4-phenyl pentane. Furthermore, the fragrance of 2-cyano-4-phenyl pentane well harmonizes with other fragrance ingredients.

What is claimed is:

1. 2-cyano-4-phenyl pentane.

2. A fragrance or perfume composition, which comprises at least two components, one component of which is an olfactorily sensible amount of 2-cyano-4-phenyl pentane, and a carrier.

3. The composition of claim 2, wherein said 2-cyano-4-phenyl pentane is present in said composition in the amount of about 0.1 to 95% by weight.

4. The composition of claim 3, wherein said 2-cyano-4-phenyl pentane is present in said composition in the amount of about 1 to 25% by weight.

5. The composition of claim 2, which further comprises another fragrance ingredient.

6. The composition of claim 5, wherein said other fragrance ingredient has a fruity, floral odor note selected from the group consisting of mughet, lilac, gardenia, rose, violet, grape-fruit and yuzu odor notes.

7. The composition of claim 6, which is:

|                      | Parts by weight |
|----------------------|-----------------|
| Hydroxycitronellal   | 20              |
| Phenyl ethyl alcohol | 15              |
| Linalyl acetate      | 10              |
| Terpineol            | 5               |
| Benzyl acetate       | 5               |
| Geraniol             | 5               |
| Linalool             | 10              |
| Citronellol          | 8               |
| Hexyl cinnamic aldehyde | 3            |
| Ylang ylang oil      | 2               |
| Geranium oil         | 2               |
| α-ionone             | 3               |
| Jasmin.absolute      | 2               |
| Heliotropine         | 2               |
| Musk ketone          | 3               |

8. The composition of claim 6, which is:

|                              | Parts by weight |
|------------------------------|-----------------|
| Methyl phenyl carbinyl acetate | 5             |
| Dimethyl benzyl carbinol     | 10              |
| Hydroxycitronellal           | 10              |
| Bergamot                     | 5               |
| Nerol                        | 5               |
| Benzyl acetate               | 10              |
| Phenyl ethyl alcohol         | 10              |
| Methyl ionone                | 5               |
| Linalool                     | 10              |
| Tolu Balsam                  | 3               |
| Heliotropine                 | 3               |
| Jassmin.absolute             | 2               |
| Rose.absolute                | 2               |
| Calbanum oil                 | 3               |
| Vetiver oil                  | 3               |
| Sandalwood oil               | 2               |
| Vanillin                     | 2               |
| Musk ketone                  | 2               |

9. The composition of claim 6, which is:

|                      | Parts by weight |
|----------------------|-----------------|
| Phenyl ethyl alcohol | 20              |
| Geraniol             | 20              |
| Citronellol          | 8               |
| Linalool             | 5               |
| Benzyl acetate       | 5               |
| α-ionone             | 3               |
| Terpineol            | 2               |
| Cinnamic alcohol     | 2               |
| Rhodinol             | 5               |
| Geranium oil         | 5               |
| Eugenol              | 2               |
| Nerol                | 3               |
| Aldehyde C-10 (10%)  | 2               |
| Nerolidol            | 5               |
| Guaiac lard          | 2               |
| Rose.absolute        | 3               |
| Musk ketone          | 3               |

10. The composition of claim 6, which is:

|                      | Parts by weight |
|----------------------|-----------------|
| Phenyl ethyl alcohol | 15              |
| Benzyl acetate       | 10              |
| Geraniol             | 5               |
| Linalool             | 5               |
| Terpineol            | 3               |
| Orange oil           | 15              |
| Lemon oil            | 10              |
| Mandarin oil         | 5               |
| Citral               | 1               |
| Petitgrain oil       | 3               |
| Aldehyde-10 (10%)    | 2               |
| Cis-3-hexane-1-ol    | 1               |
| Bergamot oil         | 2               |
| Nerol                | 2               |
| Hydroxycitronellal   | 3               |
| Methyl ionone        | 2               |
| Galbanum oil         | 1               |

* * * * *